United States Patent
Izumi et al.

(10) Patent No.: US 10,409,269 B2
(45) Date of Patent: Sep. 10, 2019

(54) OPERATION COMMAND GENERATION DEVICE, OPERATION COMMAND GENERATION METHOD, AND PROCESS

(71) Applicant: Kabushiki Kaisha Yaskawa Denki, Kitakyushu-shi (JP)

(72) Inventors: Tetsuro Izumi, Kitakyushu (JP); Hirokazu Kariyazaki, Kitakyushu (JP); Makoto Umeno, Kitakyushu (JP); Tatsuro Ipposhi, Kitakyushu (JP)

(73) Assignee: KABUSHIKI KAISHA YASKAWA DENKI, Kitakyushu-Shi, Fukuoka (JP)

( * ) Notice: Subject to any disclaimer, the term of this patent is extended or adjusted under 35 U.S.C. 154(b) by 89 days.

(21) Appl. No.: 15/667,689

(22) Filed: Aug. 3, 2017

(65) Prior Publication Data
US 2017/0329313 A1 Nov. 16, 2017

Related U.S. Application Data

(63) Continuation of application No. PCT/JP2015/053020, filed on Feb. 3, 2015.

(51) Int. Cl.
*G05B 19/418* (2006.01)
*B25J 11/00* (2006.01)
(Continued)

(52) U.S. Cl.
CPC .......... *G05B 19/4184* (2013.01); *B25J 9/009* (2013.01); *B25J 9/1661* (2013.01); *B25J 9/1666* (2013.01);
(Continued)

(58) Field of Classification Search
CPC .............. G05B 19/4184; G05B 19/418; G05B 2219/40113; G05B 2219/45092;
(Continued)

(56) References Cited

U.S. PATENT DOCUMENTS

| 5,930,461 A | 7/1999 | Bernstein et al. |
| 6,311,093 B1 * | 10/2001 | Brown .................... G05B 17/02 700/95 |

(Continued)

FOREIGN PATENT DOCUMENTS

| EP | 1666888 A2 | 6/2006 |
| JP | S64-75965 A | 3/1989 |

(Continued)

OTHER PUBLICATIONS

Search Report of Sep. 3, 2018, for corresponding EP Patent Application No. 15881076.2.

(Continued)

*Primary Examiner* — Thomas C Lee
*Assistant Examiner* — Michael Tang
(74) *Attorney, Agent, or Firm* — HEA Law PLLC

(57) ABSTRACT

Provided is an operation command generation device, which is configured to generate an operation command, which is a collection of jobs to be performed by a process system of at least a robot, based on a protocol chart of at least a plurality of process symbols, the operation command generation device circuitry includes: a job generation unit configured to generate, based on the protocol chart, a job; a priority instruction unit configured to instruct a priority condition for determining a job execution order; and an execution order determination unit configured to determine an execution order of the jobs based on the priority instructed by the priority instruction unit by using a first condition about repeatedly execution of the jobs according to the number of the containers and a second condition about execution order of the jobs according to the arrangement of the process symbols in the protocol chart.

12 Claims, 11 Drawing Sheets

(51) Int. Cl.
*C12M 1/00* (2006.01)
*B25J 9/00* (2006.01)
*B25J 9/16* (2006.01)

(52) U.S. Cl.
CPC ............ *B25J 9/1682* (2013.01); *B25J 11/00* (2013.01); *C12M 1/00* (2013.01); *G05B 19/418* (2013.01); *G05B 2219/40113* (2013.01); *G05B 2219/45092* (2013.01)

(58) Field of Classification Search
CPC ........ B25J 9/009; B25J 9/1661; B25J 9/1666; B25J 9/1682; B25J 11/00; C12M 1/00
See application file for complete search history.

(56) References Cited

U.S. PATENT DOCUMENTS

| | | |
|---|---|---|
| 2004/0208795 A1 | 10/2004 | Toi et al. |
| 2004/0210340 A1* | 10/2004 | Koike .............. G05B 19/41865 700/213 |
| 2011/0046910 A1* | 2/2011 | Haas ................ G01N 35/00871 702/108 |
| 2013/0195601 A1 | 8/2013 | Shin et al. |
| 2014/0094971 A1 | 4/2014 | Thieme et al. |
| 2015/0134110 A1 | 5/2015 | Koyanagi et al. |
| 2016/0305407 A1* | 10/2016 | Osako .................... F03D 17/00 |

FOREIGN PATENT DOCUMENTS

| | | |
|---|---|---|
| JP | 2013-157562 A | 8/2013 |
| WO | 9106050 A1 | 5/1991 |
| WO | 2014/013608 A1 | 1/2014 |

OTHER PUBLICATIONS

International Search Report of PCT/JP2015/053020 and English translation thereof.
English translation of Written Opinion of the International Searching Authority for PCT/JP2015/053020 dated Aug. 17, 2017.
Office Action dated Apr. 1, 2019, for corresponding CN Patent Application No. 201580075309. XURGENT and the English translation thereof.

* cited by examiner

_US 10,409,269 B2_

OPERATION COMMAND GENERATION DEVICE, OPERATION COMMAND GENERATION METHOD, AND PROCESS

INCORPORATION BY REFERENCE

The present disclosure contains subject matter related to that disclosed in International Patent Application under the PCT/JP2015/053020 filed in the Japan Patent Office on Feb. 3, 2015, the entire contents of which are hereby incorporated by reference.

BACKGROUND OF THE INVENTION

Field of the Invention

The present invention relates to an operational command generation device, an operation command generation method, a computer program, and a process system.

Description of the Related Art

In the fields of biochemistry and biotechnology, a work procedure and conditions of operations to be performed on a process subject, such as a series of inspections, cultivation, and amplification (those operations are hereinafter collectively referred to as "experiment"), are commonly referred to as "protocol".

SUMMARY OF THE INVENTION

According to one aspect of the present invention, there is provided an operation command generation device, which is configured to generate an operation command, which is a collection of jobs to be performed by a process system of at least a robot, based on a protocol chart of at least a plurality of process symbols each representing a process to be performed on a container in which a process subject is stored, the operation command generation device circuitry including: a job generation unit configured to generate, based on the protocol chart, a job for each process indicated by each of the plurality of process symbols; a priority instruction unit configured to instruct a priority condition, for determining a job execution order; and an execution order determination unit configured to determine, when there are a plurality of containers, an execution order of the jobs generated by the job generation unit based on the priority instructed by the priority instruction unit by using at least a first and second condition, where the first condition is that each job corresponding to each of the plurality of process symbols is to be repeatedly executed the same number of times as a count of the plurality of containers; and wherein the second condition is that each job corresponding to each of the plurality of process symbols is to be executed in an order corresponding to an arrangement order of each of the plurality of process symbols in the protocol chart.

Further, according to another aspect of the present invention, there is provided an operation command generation method for generating an operation command, which is a collection of jobs to be performed by a process system of at least a robot, based on a protocol chart of at least a plurality of process symbols each representing a process to be performed on a container in which a process subject is stored, the operation command generation method including: generating, based on the protocol chart, a job for each process indicated by each of the plurality of process symbols; instructing a priority of a condition for determining a job execution order; and determining, when there are a plurality of containers, an execution order of the jobs based on the instructed priority by using a first condition and a second condition, wherein the first condition is that each job corresponding to each of the plurality of process symbols is to be repeatedly executed the same number of times as a count of the plurality of containers; and the second condition is that each job corresponding to each of the plurality of process symbols is to be executed in an order corresponding to an arrangement order of each of the plurality of process symbols in the protocol chart.

Further, according to another aspect of the present invention, there is provided a process including: as operation command generation device which causes a computer to generate an operation command, which is a collection of jobs to be performed by a process system of at least a robot, based on a protocol chart of at least a plurality of process symbols each representing a process to be performed on a container in which a process subject is stored, the operation command generation device circuitry including: a job generation unit configured to generate, based on the protocol chart, a job for each process indicated by each of the plurality of process symbols; a priority instruction unit configured to instruct a priority condition for determining a job execution order; and an execution order determination unit configured to determine, when there are a plurality of containers, an execution order of the jobs generated by the job generation unit based on the priority instructed by the priority instruction unit by using at least a first and second condition, where the first condition is that each job corresponding to each of the plurality of process symbols is to be repeatedly executed the same number of times as a count of the plurality of containers; and wherein the second condition is that each job corresponding to each of the plurality of process symbols is to be executed in an order corresponding to an arrangement order of each of the plurality of process symbols in the protocol chart; a robot controller configured to control a control subject based on an operation command generated by the operation command generation device; and a robot configured to perform a process on a process subject with one or more arms, the robot being included in control subjects of the robot controller.

DESCRIPTION OF THE EMBODIMENTS

According to the knowledge of the inventors of the present invention, the likelihood of an anticipated result being obtained in a biochemistry or biotechnology experiment, that is, the reproducibility of the experiment, greatly depends on the competence of a person conducting the experiment, which may in some cases hinder verification of the reliability of the experiment result, for example. Accordingly, the inventors of the present invention consider excluding human factors by performing the experiment through use of a robot.

However, a common format for describing a protocol has not been established yet, and hence each experimenter is considered to describe the protocol in a unique format. Therefore, when an operation of a robot is described based on a certain protocol, for example, an engineer familiar both with the protocol and programming of the operation of the robot is necessary. Moreover, when the format for the protocol is changed, the engineer can no longer use the new format. Thus, it is practically unrealistic to describe the operation of the robot based on the protocol.

Therefore, the inventors of the present invention have invented a novel and creative operation command generation device and the like by performing extensive research and development into automatically generating an operation command for causing a robot to perform an experiment based on a protocol. This operation command generation device and the like are described below using an embodiment as an example.

Figure 1:
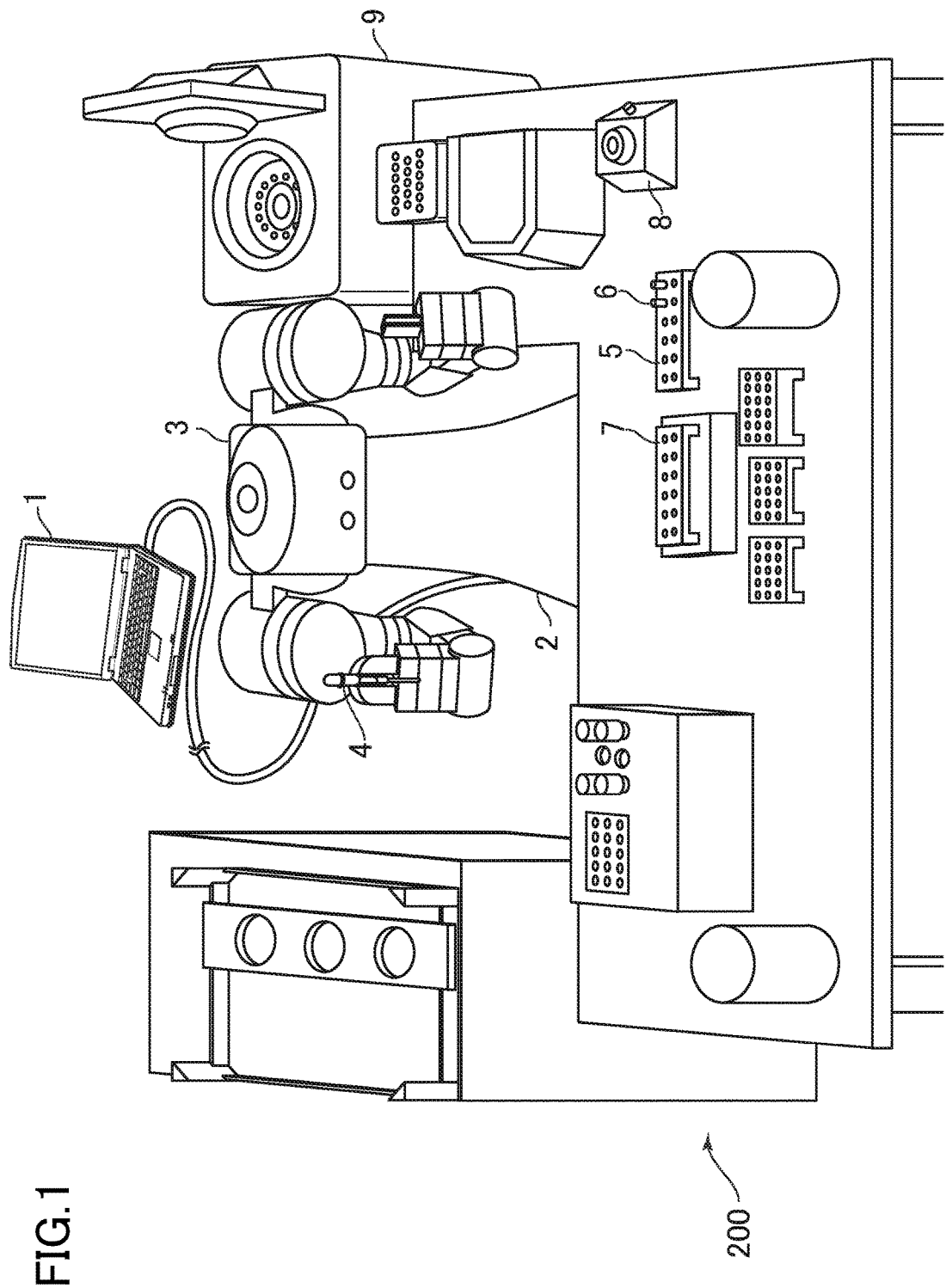
FIG. 1 is a schematic diagram for illustrating a physical configuration of a process system according to an embodiment of the present invention.

FIG. 1 is a schematic diagram for illustrating an example of a physical configuration of a process system 200 according to one embodiment of the present invention. The process system 200 includes an operation command generation device 1 configured to generate an operation command for a robot 3 based on a protocol chart for illustrating a protocol, a robot controller 2 configured to control the robot 3 based on the generated operation command, and the robot 3, which is controlled by the robot controller 2 and is configured to execute an experiment. The operation command generation device 1 itself may be a dedicated device. However, in this case, the operation command generation device 1 is realized by using a common computer. In other words, a commercially-available computer configured to execute a computer program for causing the computer to operate as the operation command generation device 1 is used for the operation command generation device 1. The computer program is in general provided in the form of application software, and is used when installed on the computer. The application software may be provided by recording the application software on a compact disc read-only memory (CD-ROM), a digital versatile disc (DVD) ROM, or another suitable computer-readable information recording medium. Further, the application software may be provided over various information communication networks, such as the Internet. In addition, the functions of the application software may be provided by a server at a remote location over an information communication network, that is, may be realized by so-called cloud computing. Still further, the robot controller 2 may be integrated with the robot 3, or in a stand-alone manner. The robot controller 2 causes the robot 3 to execute a desired operation based on an operation command generated by the operation command generation device 1.

The robot 3 is an articulated robot, which is configured to perform processes on a process subject. The robot 3 is capable of manipulating a piece of experiment equipment (which may or may not be shown) such as grasping and manipulating a pipette 4 with an arm. Further, the robot 3 is capable of moving various containers (which may or may not be shown) such as grasping a microtube 6 arranged in a tube rack 5 and moving the microtube 6 from the tube rack 5 to a main rack 7 or the like. In this embodiment, when the robot 3 is performing a process on the microtube 6, for example, injecting the process subject into the microtube 6, the robot 3 moves the microtube 6 to the main rack 7, and performs the process above the main rack 7. In the example illustrated in FIG. 1, the process system 200 further includes art agitator 8 and a centrifugal separator 5 that are examples of pieces of equipment to be used when the robot 3 performs the experiment. The process system 200 may also include other equipment in addition to or instead of those pieces of equipment. For example, the process system 200 may include a rack for storing Petri dishes, a magnet rack, and the like. Further, the robot 3 is not limited to the type that is illustrated, and the robot 3 may foe a single-arm robot or the like.

Figure 2:
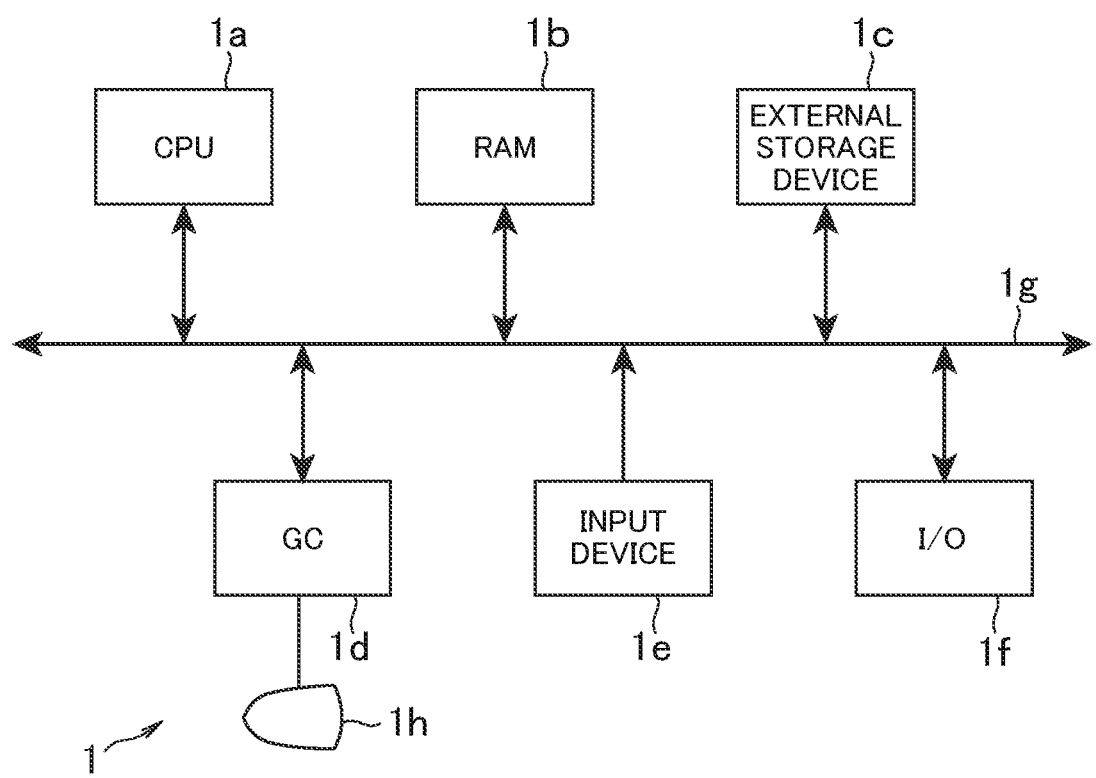
FIG. 2 is a block diagram for illustrating a physical configuration of an operation command generation device according to the embodiment of the present invention.

FIG. 2 is a block diagram for illustrating a physical configuration of the operation command generation device 1 according to the embodiment of the present invention. The configuration illustrated in FIG. 2 is a general computer used as the operation command generation device 1. In the computer, a central processing unit (CPU) 1a, a random access memory (RAM) 1b, an external storage device 1c, a graphics controller (GC) 1d, an input device 1e, and an input/output (I/O) 1f are connected to one another by a data bus 1g so that the devices can exchange electric signals therebetween. In this case, the external storage device 1c is a device capable of statically recording information, for example, a hard disk drive (HDD) or a solid state drive (SSD). Further, signals from the GC 1d are output and displayed as an image on a monitor 1h, for example, a flat panel display, which allows the user to visually recognize the image. The input device 1e is a device, for example, a keyboard, a mouse, or a touch panel, which allows the user to input information. The I/O 1f is an interface that allows the operation command generation device 1 to exchange information with an external device.

Figure 3:
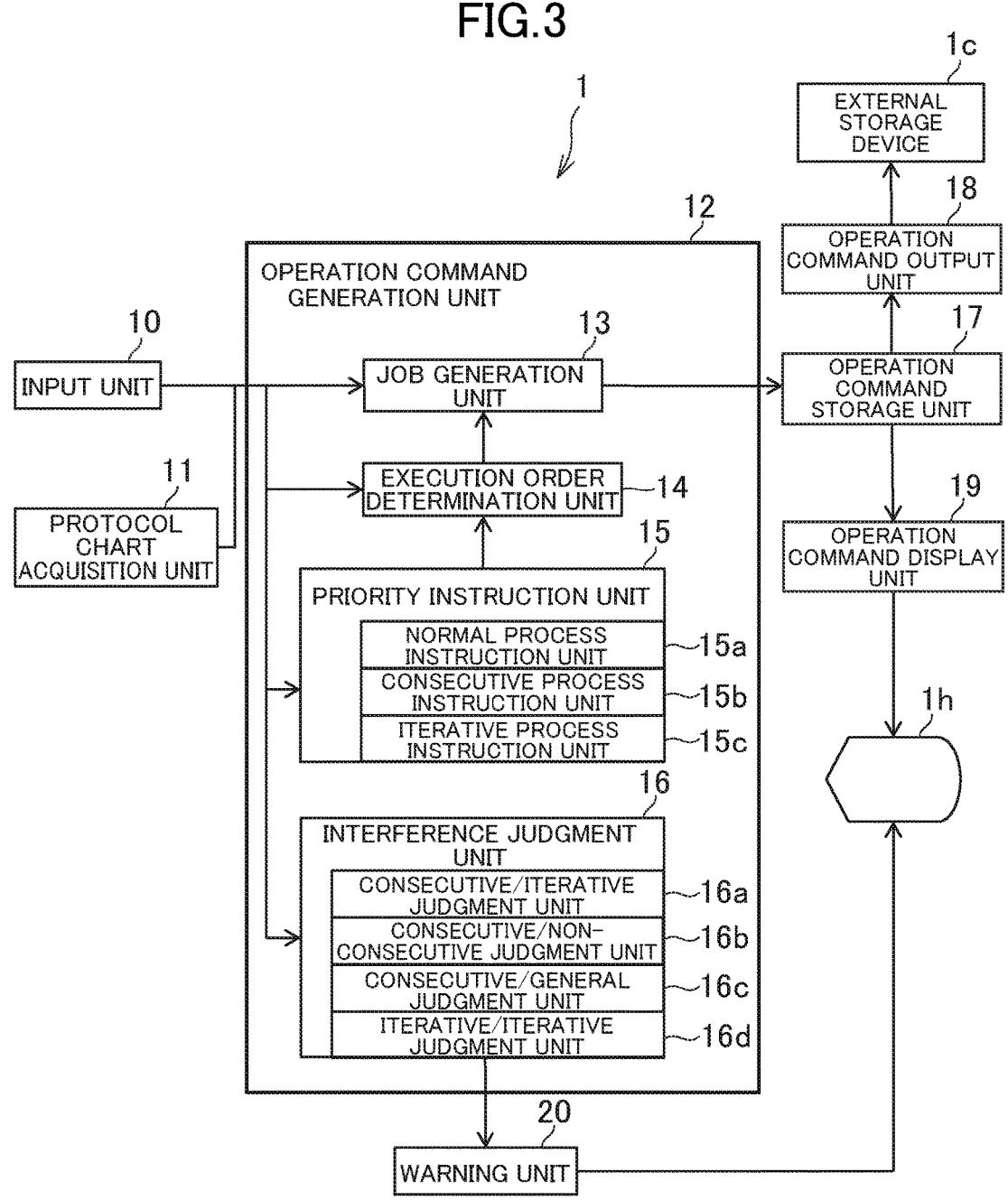
FIG. 3 is a function block diagram of the operation command generation device according to the embodiment of the present invention.

FIG. 3 is a function block diagram of the operation command generation device 1 according to this embodiment. The function blocks illustrated in FIG. 3 focus on the functions of the operation command generation device 1. It is not necessary to have a physical configuration in which each function corresponds to a function block on a one-to-one basis. Some function blocks may be realized by an information processing device, for example, the CPU 1a of the operation command generation device 1, executing specific software. Further, some function blocks may be realized by a specific storage area being allocated to an information storage device, for example, the RAM 1b of the operation command generation device 1.

The operation command generation device 1 includes an input unit 10 configured to receive various input from a user, and a protocol chart acquisition unit 11 configured to acquire a protocol chart for illustrating a protocol. Further, the operation command generation device 1 includes an operation command generation unit 12 configured to generate an operation command based on the input received by the input unit 10 and the protocol chart acquired by the protocol chart acquisition unit 11, and a warning unit 20 configured to issue a warning when the acquired protocol chart includes a predetermined description. In addition, the operation command generation device 1 includes an operation command storage unit 17 configured to store electronic data of the operation command currently being generated and operation commands that have been generated, an operation command display unit 19 configured to form the electronic data of the operation commands stored in the operation command storage unit 17 and display the formed electronic data on the monitor 1h, and an operation command output unit 18 configured to output the generated operation command as an electronic file in a format that can be read by the robot.

The input unit 10 is normally configured by the input device 1e illustrated in FIG. 2. However, when the operation command generation device 1 is an application server used in cloud computing, the I/O 1f into which operation information input by the user on a terminal at a remote location is input corresponds to the input unit 10.

The operation command generation unit 12 includes various function blocks for generating the operation command. The operation command generation unit 12 includes a job generation unit 13 configured to generate a job for each process indicated by each process symbol included in the protocol chart. The number of jobs to be generated is equal to a container count associated with the process symbol. The job generation unit 13 is described in more detail later together with the description of the generation procedure of the operation command. The operation command generation unit 12 also includes an execution order determination unit 14, a priority instruction unit 15, and an interference judgment unit 16. The execution order determination unit 14 is configured to determine an execution order of the jobs generated by the job generation unit 13 based on a priority instructed by the priority instruction unit 15. The priority instruction unit 15 is configured to specify a priority of conditions to be used when the execution order determination unit 14 determines the job execution order. The interference judgment unit 16 is configured to judge interference among the processes represented by the protocol chart.

In the present application, the term "operation command" refers to a command that, is a single job or a collection of jobs in which a plurality of jobs have been combined, for instructing a process that is recognized as a single unit to be performed on the container in which the process subject is stored. The operation command is generated by converting each symbol represented in the protocol chart into a job, which is a unit operation of the robot, and merging the converted jobs while their execution order is taken into account.

The priority instruction unit 15 includes a normal process instruction unit 15a, a consecutive process instruction unit 15b, and an iterative process instruction unit 15c. The normal process instruction unit 15a is configured to instruct, for a plurality of process symbols for which neither of a consecutive process or an iterative process, which are described later, is specified, the execution order determination unit 14 on the priority of the processes to be determined by the execution order determination unit 14 normally. The consecutive process instruction unit 15b is configured to instruct, for a plurality of process symbols for which a consecutive process is specified, the execution order determination unit 14 on a priority specific to consecutive processes. The iterative process instruction unit 15c is configured to instruct, for one or more process symbols for which an iterative process is specified, a priority specific to iterative processes.

The interference judgment unit 16 includes a consecutive/iterative judgment unit 16a, a consecutive/non-consecutive judgment unit 16b, a consecutive/general judgment unit 16c, and an iterative/iterative judgment unit 16d. The consecutive/iterative judgment unit 16a is configured to judge whether or not a group of the process symbols for which a consecutive process is specified and a group of the process symbols for which an iterative process is specified partially duplicate each other. The consecutive/non-consecutive judgment unit 16b is configured to judge whether or not one of the group of the process symbols for which a consecutive process is specified and the group of the process symbols for which a non-consecutive process is specified includes another one of the groups. The consecutive/general judgment unit 16c is configured to judge whether or not the group of the process symbols for which a consecutive process is specified and another process symbol are arranged in a direction orthogonal to the direction indicating a consecutive process. The iterative/iterative judgment unit 16d is configured to judge whether or not two groups of process symbols for which an iterative process is specified partially duplicate each other.

Figure 4:
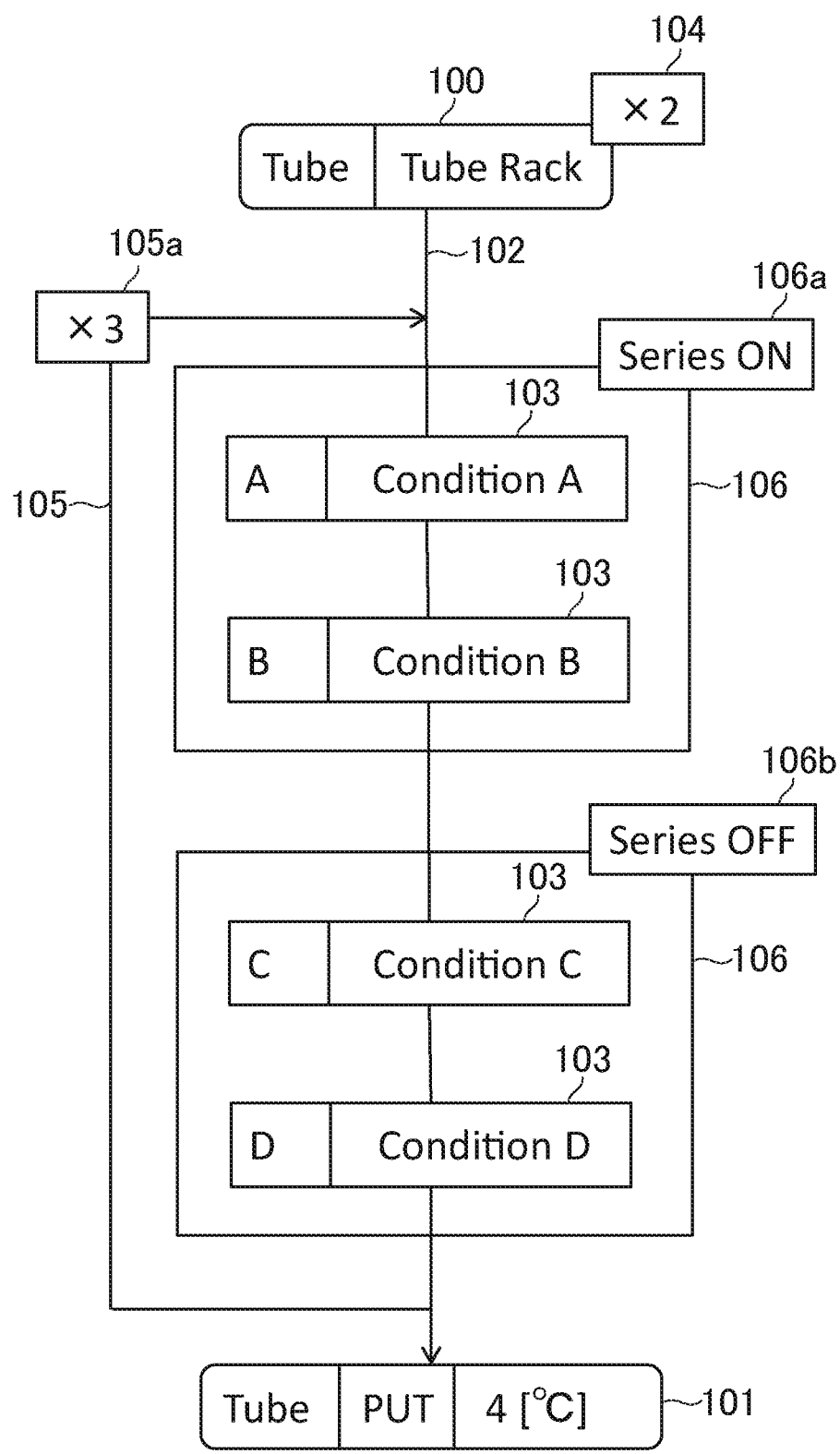
FIG. 4 is a diagram for illustrating an example of a protocol chart to be acquired by the operation command generation device according to the embodiment of the present invention.

FIG. 4 is a diagram for illustrating an example of the protocol chart to be acquired by the operation command generation device 1 according to this embodiment.

In the present application, the term "protocol chart" refers to a diagram that is illustrated in a manner that allows a protocol to be visually understood, and the term "protocol" refers to the work procedure and conditions of a pre-process and the like to be performed on a process subject in the field of biochemistry or biotechnology. Further, the term "process subject" refers to a specimen on which an experiment in the above-mentioned fields is to be performed. In general, the process subject is often a portion of biological tissue, such as a cell or DNA. The experiment is generally per formed by placing the process subject in apiece of equipment that is particularly suited to the experiment, such as a microtube (centrifuge tube), a Petri dish, or a microplate (microtiter plate). However, when the term "container" is used by itself in the present application, the term refers to all of those pieces of equipment suitable for containing the process subject in the experiment.

Further, for convenience, the upward direction in FIG. 4 is referred to as a first direction, and the direction intersecting the first direction is referred to as a second direction. It is not necessary for the angle of intersection between the first direction and the second direction to be a right angle. However, in this case, the first direction and the second direction are perpendicular to each other. As a result, the second direction is the horizontal direction in FIG. 4.

In the protocol chart of this example, basically, an initial symbol 100 representing an initial state of the container containing the process subject and a final symbol 101 representing a final state of the container are arranged in the first direction. The initial symbol 100 and the final symbol 101 are connected in the first direction by a procedure line 102 heading from the initial symbol 100 to the final symbol 101. A process symbol 103 representing an individual process to be performed on the container is arranged along the procedure line 102. In the first example illustrated in FIG. 4, there are illustrated the initial symbol 100 and the final symbol 101 in which "Tube" is written and a plurality of process symbols 103 associated with the procedure line 102 connecting the initial symbol 100 and the final symbol 101. In this case, the procedure line 102 represents the procedure in which the processes are to be performed as an arrow line. A container count symbol 104 in which "×2" is written is displayed while being superimposed on the initial symbol 100. The container count symbol 104 is arranged to be superimposed on the initial symbol 100, and thus the association of the initial symbol 100 with the plurality of process symbols connected by the procedure line 102 is clearly shown. The container count symbol 104 represents that the process indicated by the process symbol 103 is to be performed on two containers. Specifically, the protocol chart of this example represents a protocol in which the processes indicated by the plurality of process symbols 103 are performed on two microtubes.

In the protocol chart of this example, a process symbol 103 in which "A" is written, a process symbol 103 in which "B" is written, a process symbol 103 in which "C" is written, and a process symbol 103 in which "D" is written are illustrated in order from the initial symbol 100 side. For example, the process symbol 103 in which "A" is written indicates that a process A is to be performed under a condition A on a microtube. Specific examples of the process include a process of adding a chemical solution into a microtube, a process of transferring contents between microtubes, and a scraping process for acquiring cells cultivated on a Petri dish.

Among the plurality of process symbols 103, the process symbol 103 in which "A" is written and the process symbol 103 in which "B" is written are surrounded by a group symbol 106*a* on which a consecutive process symbol 106*a* in which "Series ON" is displayed is superimposed to indicate that those process symbols 103 are a group of the process symbols for which a consecutive process is specified. The process symbol 103 in which "C" is written and the process symbol 103 in which "D" is written are surrounded by a group symbol 106 on which a non-consecutive process symbol 106*b* in which "Series OFF" is displayed is superimposed to indicate that those process symbols 103 are a group of the process symbols for which a non-consecutive process is specified.

The group symbol 106 indicates a group of process symbols obtained by bundling a group of the process symbols 103 into one group. The group symbol 106 is used when the user writing the protocol chart describes a user-defined process by gathering individual processes. The consecutive process symbol 106*a* represents that the processes indicated by the group of the process symbols for which a consecutive process is specified are to be performed in series on each container. The non-consecutive process symbol 106*b* represents that the processes (non-consecutive processes) indicated by the group of the process symbols for which a non-consecutive process is specified are to be performed in parallel on all the containers for each process.

The protocol chart of this example includes an iteration line 105 and an iteration count symbol 105*a* in which "×3" is displayed. The iteration count symbol 105*a* is superimposed on the iteration line 105. The iteration line 105 represents that the processes indicated by the process symbols 103 included in a range specified by the iteration line 105 are to be repeatedly performed the same number of times as the number indicated by the iteration count symbol 105*a* (iterative processing). In the case of this example, the iteration line 105 and the iteration count symbol 105*a* represent that Processes A, B, C, and D are to foe repeated three times. In the protocol chart of this example, it is represented by the container count symbol 104 that Processes A, B, C, and D are to be performed on two micro tubes, and hence, together with the iteration line 105 and the iteration count symbol 105*a*, the protocol chart represents that Processes A, B, C, and D are to foe performed three times on each of the two microtubes.

As illustrated in the protocol chart of this example, an iterative process can be specified together with a consecutive process or a non-consecutive process. A plurality of iteration lines 105 may be arranged for one procedure line 102, and the group symbol 106 may include process symbols 103 that are surrounded by one or more group symbols 106. However, when an iterative process and a consecutive process are specified together, it is necessary to specify the processes so that those processes do not interfere with each other. When a plurality of iterative processes are specified, it is necessary to specify the iterative processes so that those iterative processes do not interfere with each other. When a group symbol 106 surrounds another group symbol 106, it is necessary to specify individual processes so that there is no interference among the consecutive processes and the non-consecutive processes. It is also necessary to specify individual, processes so that other general processes do not interfere with the consecutive processes. Those interference judgements are described in more detail later.

In this embodiment, the job generation unit 113*d* is configured to generate jobs for causing the process system 200 to perform the processes indicated by the process symbols 103. The number of jobs to be generated is equal to the container count associated with the process symbols 103 (container count indicated by the container count symbol 104). The job generation unit 13 is also configured to repeatedly generate job(s) for the one or more process symbols 103 for which an iterative process is specified. In this case, the number of jobs to be generated is equal to the iteration count (iteration count indicated by the iteration count symbol 105*a*). Therefore, the job generation unit 13 is configured to generate, for one process symbol 103, a number of jobs equal to the product of the container count associated with that process symbol 103 and the iteration count specified by that process symbol 103. In this embodiment, the execution order determination unit 14 is configured to determine the execution order of the jobs generated by the job generation unit 13 based on the priority instructed by the priority instruction unit 15 by using the following conditions: [1] that each job corresponding to each of the plurality of process symbols is to be repeatedly executed the same number of times as the container count; [2] that each job corresponding to each of the plurality of process symbols is to be executed in an order corresponding to an arrangement order of each of the plurality of process symbols 103 in the protocol chart; and [3] that a job corresponding to a process symbol 103 for which an iterative process is specified is to be repeatedly executed the same number of times as a collectively-specified iteration count. The priority instruction unit 15 is configured to instruct the execution order determination unit 14 on the priority of each condition.

The normal process instruction unit 15a is configured to instruct that the condition [1] takes priority over the condition [2] for the plurality of process symbols 103 for which neither a consecutive process nor an iterative process is specified. In contrast, the consecutive process instruction unit 15b is configured to instruct the execution order determination unit 14 to prioritize the condition [2] over the condition [1] for the plurality of process symbols 103 for which a consecutive process is specified. The iterative process instruction unit 15c is configured to instruct the execution order determination unit 14 to prioritize the conditions [1] and [2] over the condition [3] for the one or more process symbols 103 for which an iterative process is specified. Those functions of the operation command generation device 1 according to this embodiment are now described with reference to FIG. 5.

Figure 5:
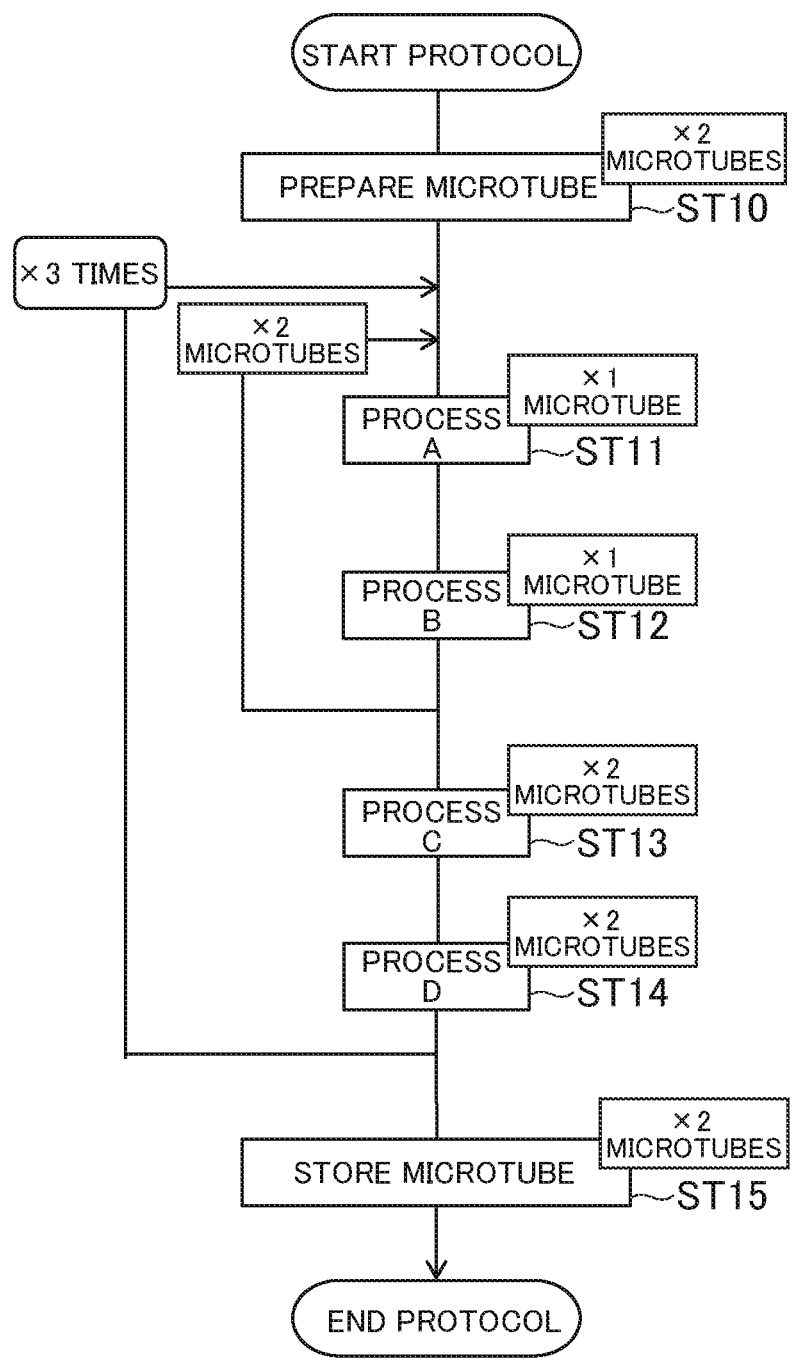
FIG. 5 is a conceptual diagram for illustrating an operation command to be generated by the operation command generation device according to the embodiment of the present invention based on the protocol chart illustrated in FIG. 4.

FIG. 5 is a conceptual diagram for illustrating an operation command to be generated by the operation command generation device 1 according to the embodiment of the present invention based on the protocol chart illustrated in FIG. 4. The operation command generation device 1 according to this embodiment acquires the protocol chart illustrated in FIG. 4 by using the protocol chart acquisition unit 11, and generates a job for causing the process system including the robot 3 to first perform the process indicated by the initial symbol 100 (ST10). The initial symbol 100 represents a process for arranging the microtube 6 stored in the tube rack 5 in the main rack 7. In this case, in accordance with the container count symbol 104, a job is generated for causing two microtubes 6 to be arranged in the main rack 7. The job generation unit 13 generates a job for causing the robot 3 included in the process system 200 to repeatedly perform, while offsetting by the arrangement position of the microtubes 6, an operation on the two microtubes 6 in which a microtube 6 is moved from the tube rack 5 and arranged in the main rack 7.

Next, based on the process symbol 103 in which "A" is written and the process symbol 103 in which "B" is written, the job generation unit 13 generates jobs for causing the process system 200 to perform Processes A and B. The number of jobs to be generated is equal to the container count associated with the process symbols 103 (i.e., two, which is the container count indicated by the container count symbol 104). At this point, when neither a consecutive process nor an iterative process is specified for the process symbol 103, the execution order determination, unit 14 determines: the job execution order by prioritizing the condition [1] over the condition [2] in accordance with an instruction from the normal process instruction unit 15a. The job for causing Process A to be performed and the job for causing Process B to be per termed are each performed on two micro tubes 6, and hence two jobs correspond to one process symbol 103 (i.e., correspond to the process symbol 103 in which "A" is written or the process symbol 103 in which "B" is written). Therefore, in principle, execution of Processes A and B on the two microtubes 6 is prioritized over the arrangement position of the process symbol 103, and thus the jobs are generated in an execution order of causing Process A to be performed on the two microtubes 6, and then Process B to be performed on the two microtubes 6.

However, in the protocol chart illustrated in FIG. 4, the process symbol 103 in which "A" is written and the process symbol 103 in which "B" is written are a plurality of process symbols 103 for which a consecutive process is specified.

Therefore, the consecutive process instruction unit 15b instructs the execution order determination unit 14 to prioritize the condition [2] over the condition [1]. Specifically, the consecutive process instruction unit 15b prioritizes executing the jobs corresponding to each of the plurality of process symbols in an order corresponding to the arrangement order of the process symbols 103, namely, the arrangement order in which the process symbol 103 in which "A" is written is arranged on the initial symbol 100 side (i.e., upstream side of the procedure line 102) and the process symbol 103 in which "B" is written is arranged on the final symbol 101 side (i.e., downstream side of the procedure line 102), over repeatedly executing the two jobs corresponding to the one process symbol 103 the same number of times as the container count (i.e., 2). As a result, the job generation unit 13 generates a job for repeating on the two microtubes 6 the job for causing the process system 300 to perform Process A (ST11) and Process B (ST12) on a single microtube 6.

Next, based on the process symbol 103 in which "C" is written and the process symbol 103 in which "D" is written, the job generation unit 13 generates jobs for causing the process system 200 to perform Processes C and D. The number of jobs to be generated is equal to the container count associated with the process symbols 103 (i.e., two, which is one container count indicated by one container count symbol 104). In this case, the process symbol 103 in which "C" is written and the process symbol 103 in which "D" is written are a group of the process symbols 103 for which a non-consecutive process is specified, for those process symbols 103, and hence the job execution order is determined by prioritizing execution of Processes C and D on the two microtubes 6, as instructed by the normal process instruction unit 15a. As a result, the job generation unit 13 generates a job for causing the process system 200 to perform Process C on the two microtubes 6 (ST13) and a job for causing the process system 200 to perform Process D on the two microtubes 6 (ST14).

The process symbols 103 in which "A" to "D" are written, respectively, are process symbols for which an iterative process is specified. The iteration count for those iterative processes is 3, and hence the job generation unit 13 repeatedly generates jobs; corresponding to each process symbol the same number of times as that iteration count. The iterative process instruction unit 15c instructs the execution order determination unit 14 to prioritize the conditions [1] and [2] over the condition [3]. As a result, for example, for a job whose iteration count is 1, the execution order of the generated jobs is determined based on the conditions [1] and [2] within that iteration count. As described above, which of the conditions [1] and [2] is to be prioritized is determined based on whether an instruction is issued from the normal process instruction unit 15a or the consecutive process instruction unit 15b. When the order has been determined such that execution of all of the jobs belonging to that iteration count are performed, then the execution order of the jobs belonging to the next iteration count is similarly determined. In this way, the jobs corresponding to the process symbols for which an iterative process is specified are repeatedly executed the same number of times as the collectively-specified iteration count.

Lastly, based on the final symbol 101, the job generation unit 13 generates a job for causing the process system 200 to store the two microtubes 6 in a thermostatic bath of 4° C. (ST15).

Figure 6:
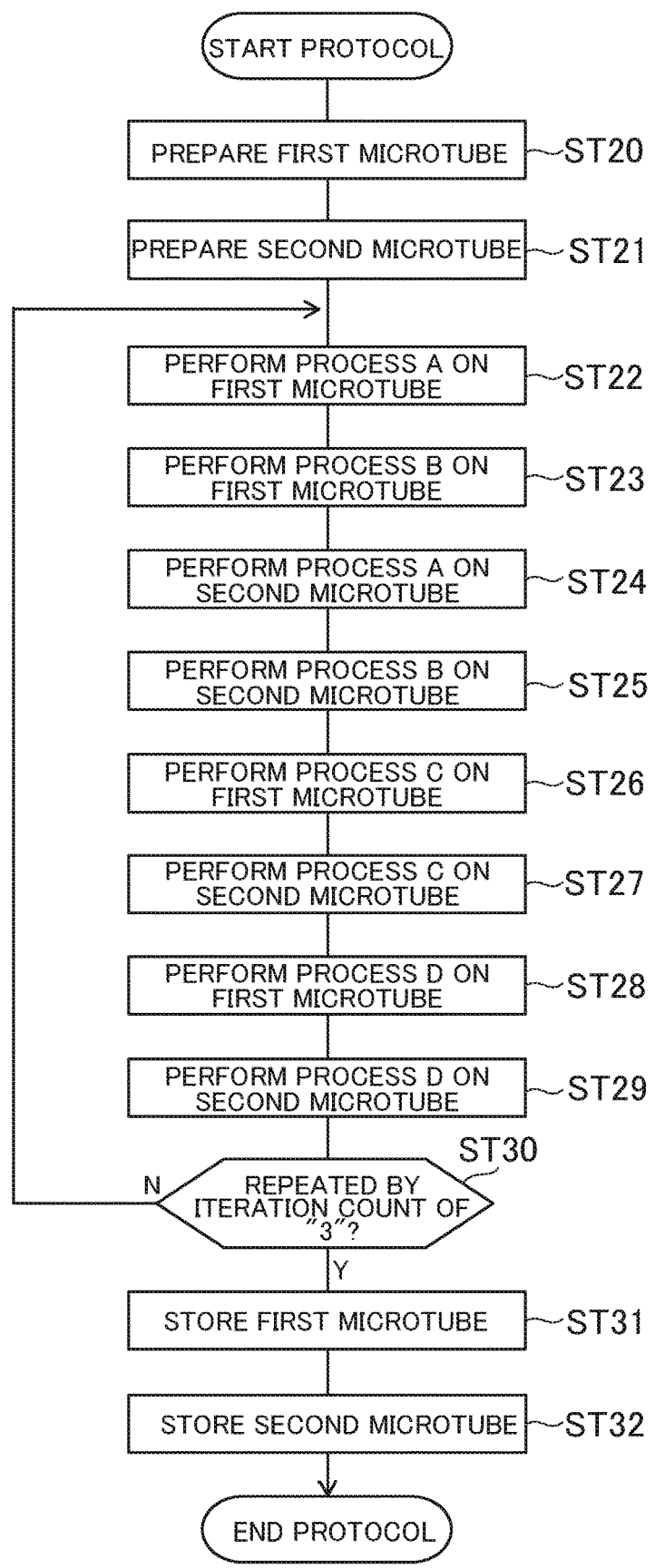
FIG. 6 is a flowchart of an operation command to be generated by the operation command generation device according to the embodiment of the present invention based on the protocol chart illustrated in FIG. 4.

FIG. 6 is a flowchart of the operation command to be generated by the operation command generation device 1 according to the embodiment of the present invention based on the protocol chart illustrated in FIG. 4. The operation command to be generated based on the protocol chart illustrated in FIG. 4 starts from a job for causing a first microtube (first microtube 6 stored in the tube rack 5) to be moved from the tube rack 5 and arranged in the main rack 7 (ST20). Next, a job for causing a second microtube (second microtube 6 stored in the tube rack 5) to be moved from the tube rack 5 and arranged in the main rack 7 is executed (ST21).

Then, for Processes A and B for which a consecutive process is specified, a job for causing Process A to be performed on the first microtube is executed (ST22), and a job for causing Process B to be performed on the first microtube is executed (ST23). Next, a job for causing Process A to be performed on the second microtube is executed (ST24), and a job for causing Process B to be performed on the second, microtube is executed (ST25).

Then, for Processes C and D for which a non-consecutive process is specified, a job for causing Process C to be performed on the first microtube is executed (ST26), and a job for causing Process C to be performed on the second microtube is executed (ST27). Next, a job for causing Process D to be performed on the first microtube is executed (ST28), and a job for causing Process D to be performed on the second microtube is executed (ST29).

Then, it is judged whether or not Processes A to D have been repeatedly performed three times, which is the iteration count, on the two microtubes 6 (ST30). When those processes have not been performed three times, a job for causing the processing of Steps ST22 to ST29 to be performed is executed. When it is judged that Processes A to D have been repeatedly performed three times, a job is executed that causes a process for storing the first microtube in a predetermined position to be performed (ST31), and a job is executed that causes a process for storing the second microtube in a predetermined position to be performed (ST32).

The jobs to be generated by the job generation unit of this embodiment include: a first level job including a command for repeating, the same number of times as a container count, the group of processes for which a consecutive process is specified, and a command for repeating, the same number of times as an iteration count, the group of processes for which an iterative process is specified; and a second level job including a command for repeating, the same number of times as the container count, individual processes other than the group of processes for which a consecutive process is specified and a command for performing once the group of processes for which a consecutive process is specified.

Figure 7:
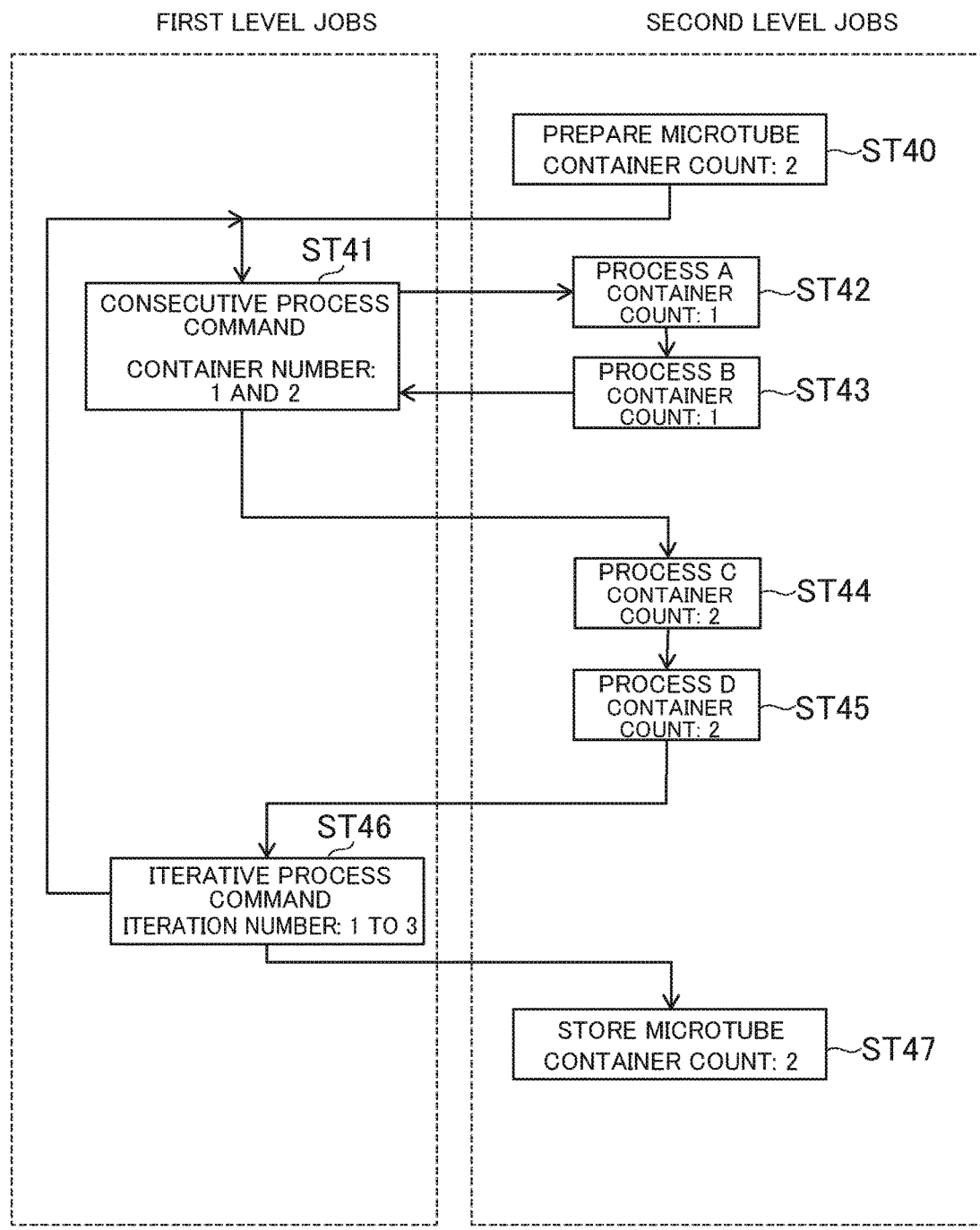
FIG. 7 is a diagram for illustrating a flow of jobs generated at an intermediate-stage when the operation command generation device according to the embodiment of the present invention generates a flow of the operation command illustrated in FIG. 6 based on the protocol chart illustrated in FIG. 4.

FIG. 7 is a diagram for illustrating a flow of jobs generated at an intermediate stage when the operation command generation device 1 according to the embodiment of the present invention generates a flow of the operation command illustrated in FIG. 6 based on the protocol chart illustrated in FIG. 4. In this embodiment, the protocol chart is smoothly converted into an operation command by dividing the jobs into the first level jobs and the second level jobs to form a hierarchical structure. In FIG. 7, in order to illustrate the hierarchical structure of the jobs, the first level jobs are illustrated on the left side, and the second level jobs are illustrated on the right side.

Firstly, the initial symbol 100 included in the protocol chart of FIG. 4 is converted into a job for preparing the microtubes as a second level job (ST40). In this case, the fact that the container count is 2 means that this job is to be converted into an operation command to be repeatedly performed on two containers. In contrast, the consecutive process symbol 105a is converted into a consecutive process command, which is a first level job (ST41). The consecutive process command indicates that the second level jobs belonging to the consecutive process command are to be repeated on container numbers 1 and 2. In this case, the second level jobs belonging to the consecutive process command are the job for causing Process A to be performed (ST42) and the job for causing Process B to be performed (ST43), and because the container count of those processes is 1, the operation is not repeated on a plurality of containers. The container number on which Processes A and B are to be performed is specified by the consecutive process command. Specifically, the consecutive process command is a command for specifying the order of the container numbers, and repeatedly calling the second level jobs that have a container count of 1. Processes A and B are called in order based on the consecutive process command for the container number 1, and then called in order for the container number 2. In this way, the order of the consecutive processes is determined.

The jobs for causing Processes C and D to be performed are executed based on a normal process order, and hence those jobs are each described as second level jobs having a container count of 2, and converted into an operation command (ST44 and ST45).

The iterative process command (ST46) is a command for returning the processes to the top of the range for which an iterative process is specified in accordance with the iteration count. The iterative process command indicates that the second level jobs belonging to the iterative process command are repeated for iteration counts of 1 to 3. In this case, the second level jobs belonging to the iterative process command are Processes A and B for which a consecutive process is specified and Processes C and D, which are normal processes. As a result, the second level jobs in the range for which an iterative process is specified repeatedly appear the same number of times as the iteration count, and the order of the iterations is determined.

Lastly, the final symbol 101 is converted into a job for storing the microtubes as a second level job (ST47). In this case, the fact that the container count is 2 means that this job is to be converted into an operation command to be repeatedly performed on two containers.

As described above, the first level jobs are commands that are indirectly converted into operation commands by calling a second level job, and the second level jobs are commands that are directly converted into jobs for the robot 3. In this way, through employment of a data structure formed in a hierarchy, that hierarchical structure can be utilized to implement advanced control of consecutive processes and iterative processes without adding second level jobs prepared as a command group to be directly converted into operation commands.

The job generation unit 13 of this embodiment includes a consecutive process job generation unit, an iterative process job generation unit, and an individual process job generation unit. The consecutive process job generation unit is configured to generate jobs for causing the process system 200 to repeat the processes indicated by a plurality of process symbols 103 for which a consecutive process is specified the same number of times as the container count (i.e., number represented by the container count symbol 104). The iterative process job generation unit is configured to generate jobs for causing the process system 200 to repeat the processes indicated by one or more process symbols 103 for which an iterative process is specified the same number of times as the iterative count (i.e., iteration count symbol 105a). The individual process job generation unit is configured to generate a job fox causing the process system 200 to repeat the processes indicated by the process symbols 103 for which a consecutive process is not specified the same number of times as the container count, and to generate a job for causing the process system 200 to perform once the processes indicated by the process symbols 103 for which a consecutive process is specified. As a result, jobs formed into a hierarchy of first level jobs and second level jobs are generated by the job generation unit 13, and systematic job generation is performed. Thus, job management becomes easier.

As described later, the job execution order of process symbols 103 having the same arrangement position in the first direction of the protocol chart is determined based on the arrangement position in the second position. In the case of the execution order determination unit 14 of this embodiment, the job execution order is determined so that the process of a process symbol 103 arranged on the left of the protocol chart is prioritized.

With the operation command generation device 1 according to this embodiment, operation commands that allow the robot 3 to operate efficiently are automatically generated when the same process is to be repeated on a plurality of containers. When the same process is to be repeated on a plurality of containers, operation commands for repeating the same process the same number of times as the container count are automatically generated by offsetting the arm position of the robot 3 for each container. Operation commands for causing the consecutive processes to be performed on each container are also automatically generated based on the protocol chart, which includes a plurality of process symbols 103 for which a consecutive process is specified.

With the operation command generation device 1 according to this embodiment, operation commands for causing iterative processes to be performed are automatically generated based on the protocol chart, which includes one or more process symbols 103 for which an iterative process is specified. The iterative processes are represented by arranging the iteration line 105 and the iteration count symbol 105*a* in the protocol chart. With the operation command generation device 1 according to this embodiment, the operation commands for causing iterative processes to be performed are automatically generated based on a protocol chart that has been written in a simple manner by using the iteration line 105 and the iteration count symbol 105*a*.

Figure 8:
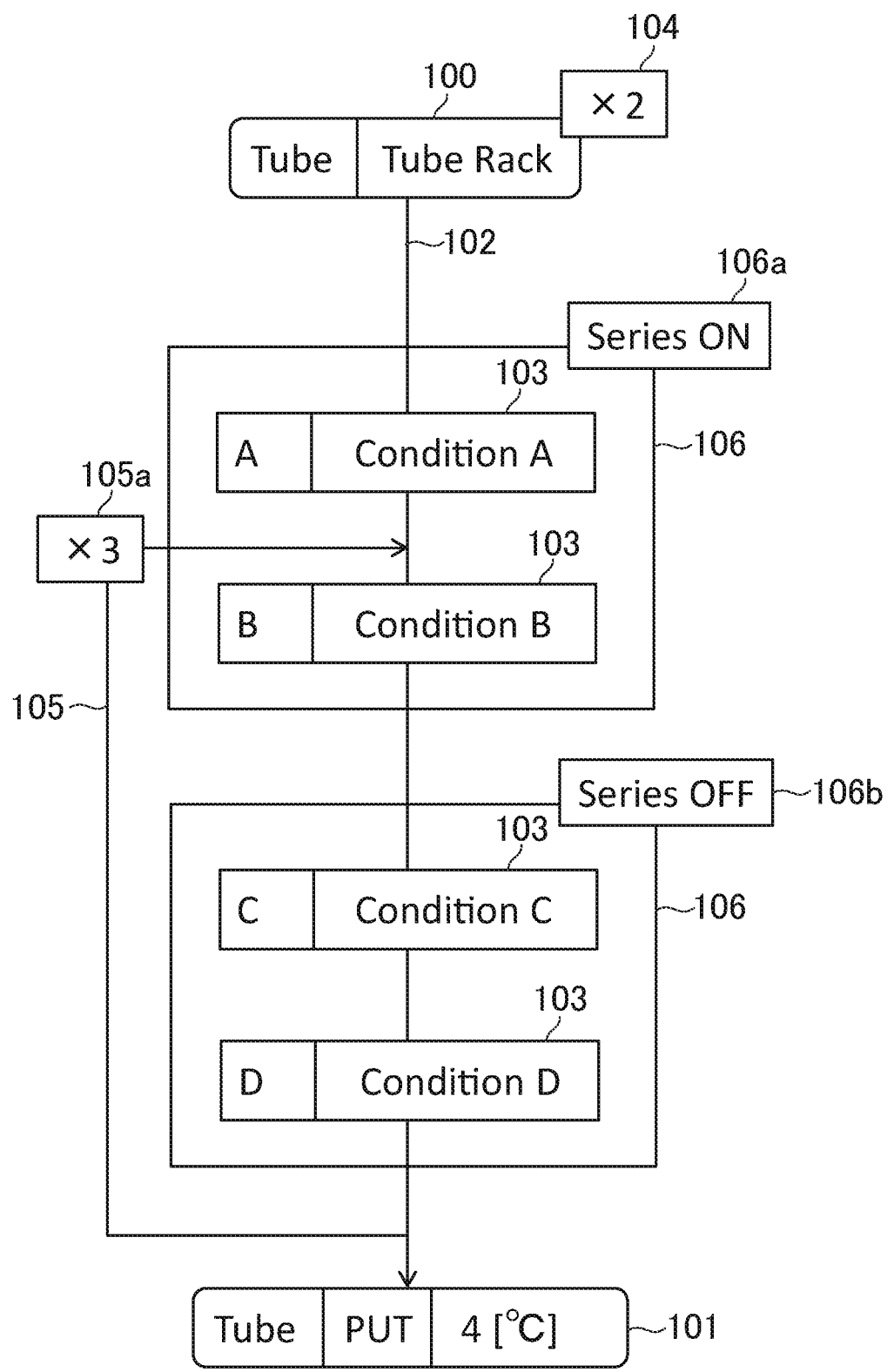
FIG. 8 is a diagram for illustrating a first example of a protocol chart on which a warning is to be displayed by the operation command generation device according to the embodiment of the present invention.

FIG. 8 is a diagram for illustrating a first example of a protocol chart on which a warning is to be displayed by the operation command generation device 1 according to the embodiment of the present invention. In the protocol chart illustrated in FIG. 8, the iteration line 105 is arranged between the process symbol 103 in which "A" is written and the process symbol 103 in which "B" is written. On the other hand, in the protocol chart illustrated in FIG. 4, the iteration line 105 is arranged between the initial symbol 100 and the process symbol 103 in which "A" is written.

In the protocol chart of the first example, the iteration line 105 is arranged between the group of the process symbols 103 for which a consecutive process is specified (i.e., between the process symbol 103 in which "A" is written and the process symbol 103 in which "B" is written). As a result, after Processes A, B, C, and D have been performed once, Process B and the following processes are repeated. However, Processes A and B are processes for which a consecutive process is specified, and hence execution of Process B alone is incompatible with this specification as a consecutive process.

The consecutive/iterative judgment unit 16*a* of this embodiment is configured to judge, based on the protocol chart acquired by the protocol chart acquisition unit 11, whether or not the group of the process symbols for which a consecutive process is specified and the group of the process symbols for which an iterative process is specified partially duplicate each other. In the case of the protocol chart of the first example, the consecutive/iterative judgment unit 16*a* judges that the group of the process symbols for which a consecutive process is specified (i.e., the process symbol 103 in which "A" is written and the process symbol 103 in which "B" is written) and the group of the process symbols for which an iterative process is specified (i.e., the process symbol 103 in which "B" is written, the process symbol 103 in which "C" is written, and the process symbol 103 in which "D" is written) partially duplicate each other in terms of the process symbol 103 in which "B" is written.

In response to the judgment by the consecutive/iterative judgment unit 16*a*, the warning unit 20 warns the user of the operation command generation device 1. The warning is performed by, for example, displaying a warning message on the monitor 1*h*.

The warning unit 20 of this embodiment is configured to issue a warning when the job generation unit 13 generates a job. The timing for issuing a warning by the warning unit 20 may not always be the time when the operation command generation device 1 generates an operation command to be read into the robot controller 2, but may also be the time when the operation command generation device 1 simulates generation of an operation command based on the protocol chart.

With the operation command generation device 1 according to this embodiment, interference between the consecutive processes and the iterative processes is prevented by issuing a warning when the specification of the consecutive processes and the specification of the iterative processes are incompatible. In response to the warning of interference between the consecutive processes and the iterative processes, the user of the operation command generation device 1 can edit the protocol chart to write a protocol that does not have any contradictions. The user of the operation command generation device 1 can also freely edit the protocol chart, without unnecessary warnings until a job is generated.

Figure 9:
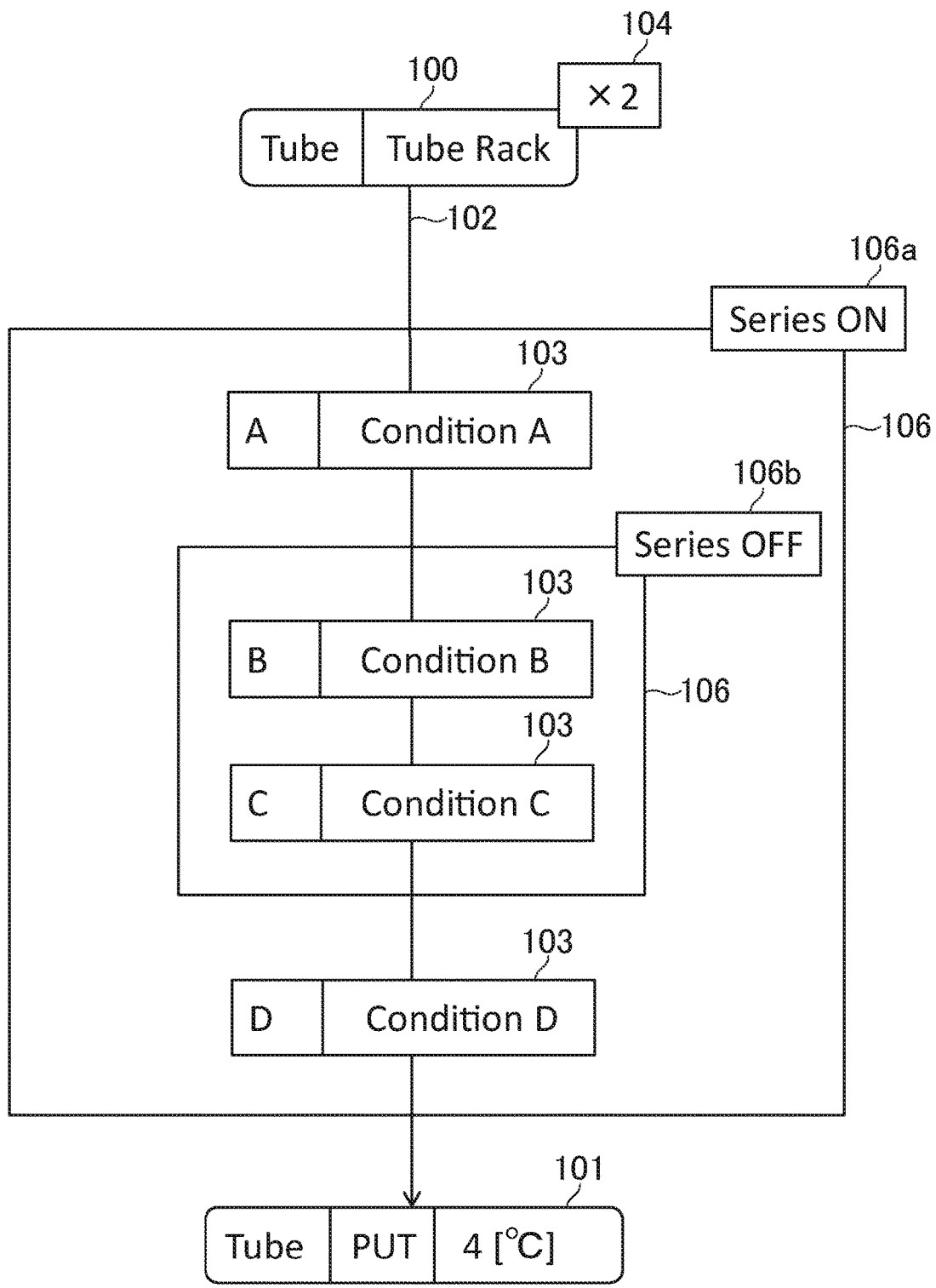
FIG. 9 is a diagram for illustrating a second example of a protocol chart on which a warning is to be displayed by the operation command generation device according to the embodiment of the present invention.

FIG. 9 is a diagram for illustrating a second example of a protocol chart on which a warning is to be displayed by the operation command generation device 1 according to the embodiment of the present invention. In the protocol chart illustrated in FIG. 9, the group symbol 106 associated with the non-consecutive process symbol 106*b* is arranged in the group symbol 106 associated with the consecutive process symbol 106*a*.

In the protocol chart of the second example, the group of the process symbols 103 for which a consecutive process is specified (i.e., the process symbol 103 in which "A" is written, the process symbol 103 in which "B" is written, the process symbol 103 in which "C" is written, and the process symbol 103 in which "D" is written) includes the group of the process symbols 103 for which a non-consecutive process is specified (i.e., the process symbol 103 in which "B" is written and the process symbol 103 in which "C" is written). Therefore, for the process symbol 103 in which "B" is written and the process symbol 103 in which "C" is written, the specification as a consecutive process and the specification as a non-consecutive process are incompatible.

The consecutive/non-consecutive judgment unit 16b of this embodiment is configured to judge, based on the protocol chart acquired by the protocol chart acquisition unit 11, whether or not one of the group of the process symbols for which a consecutive process is specified and the group of the process symbols for which a non-consecutive process is specified includes another one of the groups. In the case of the protocol chart of the second, example, the consecutive/non-consecutive judgment unit 16b judges that among the group of the process symbols for which a consecutive process is specified (i.e., the process symbol 103 in which "A" is written and the process symbol 103 in which "B" is written, the process symbol 103 in which "C" is written, and the process symbol 103 in which "D" is written) and the group of the process symbols for which an iterative process is specified (i.e., the process symbol 103 in which "B" is written and the process symbol 103 in which "C" is written), the group of the process symbols for which a consecutive process is specified includes the group of the process symbols for which a non-consecutive process is specified.

In response to the judgment by the consecutive/non-consecutive judgment unit 16b, the warning unit 20 warns the user of the operation, command generation device 1 by, for example, displaying a warning message on the monitor 1h. The warning unit 20 may issue the warning when the job generation unit 13 generates a job.

With the operation command generation device 1 according to this embodiment, interference between the consecutive processes and the non-consecutive processes is prevented by issuing a warning when the specification of the consecutive processes and the specification of the non-consecutive processes are incompatible. In response to the warning of interference between the consecutive processes and the non-consecutive processes, the user of the operation command generation device 1 can edit the protocol chart to write a protocol that does not have any contradictions. The user of the operation command generation device 1 can also freely edit the protocol chart without unnecessary warnings until a job is generated.

Figure 10:
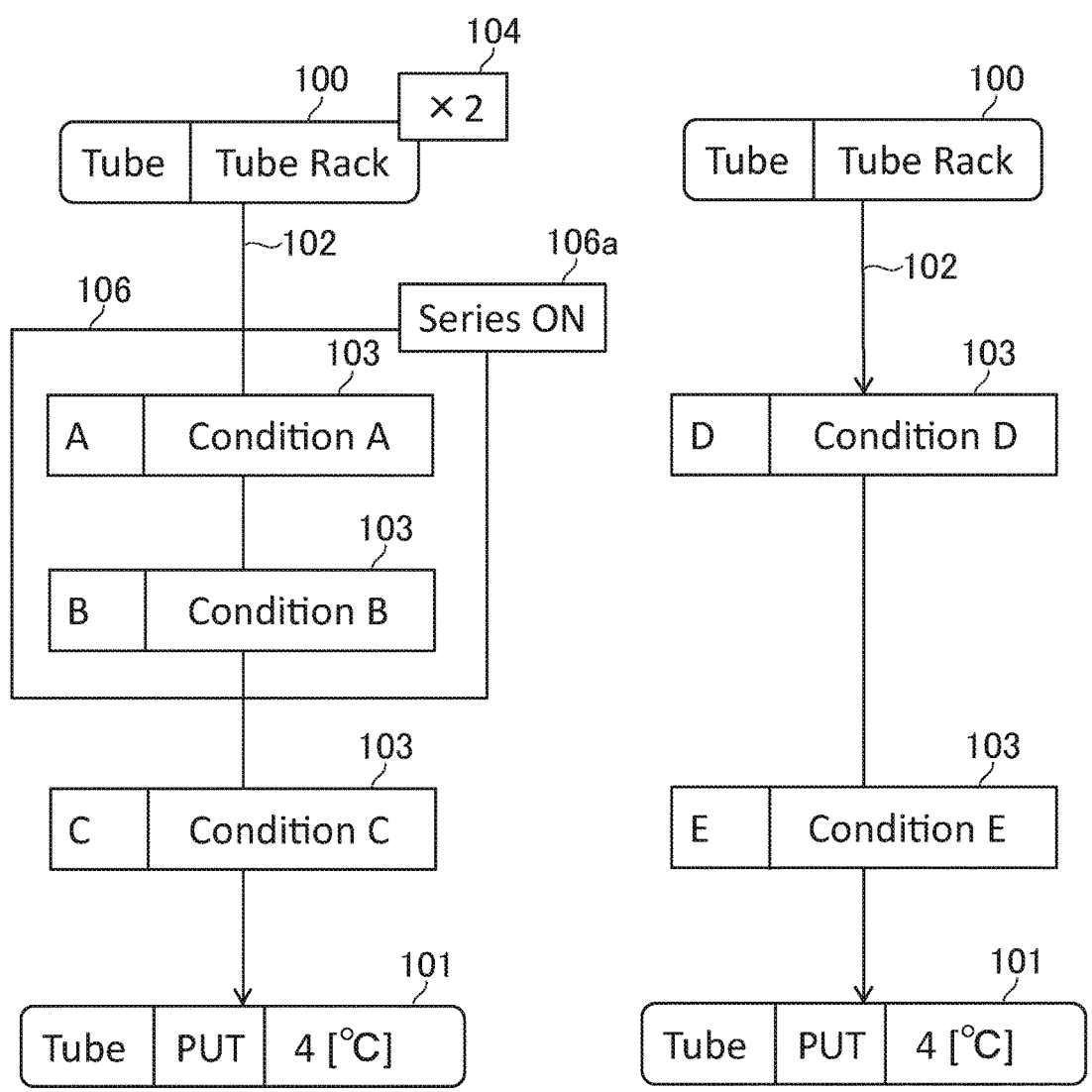
FIG. 10 is a diagram for illustrating a third example of a protocol chart on which a warning is to be displayed by the operation command generation device according to the embodiment of the present invention.

FIG. 10 is a diagram for illustrating a third example of a protocol chart on which a warning is to be displayed by the operation command generation device 1 according to the embodiment of the present invention. The protocol chart illustrated in FIG. 10 represents a protocol in which Processes A and B are consecutively performed on each of two microtubes and then Process C is performed on each of the two microtubes, and a protocol in which Processes D and E are performed on one microtube.

The operation command generation device 1 according to this embodiment is configured to refer to the arrangement position of the process symbols 103 in the protocol chart when the job execution order is determined by the execution order determination unit 14. When a plurality of process symbols 103 are arranged in the same position in the first direction (i.e., direction indicating a consecutive process, which is the vertical direction of FIG. 10), the execution order determination unit 14 determines the job execution order based on the arrangement position in the second direction (i.e., direction orthogonal to the first direct ion, namely, the horizontal direction of FIG. 10). Specifically, the operation command generation device 1 according to this embodiment determines the job execution order so that the processes indicated by process symbols 103 arranged on the left side of the protocol chart are performed first. As a result, of Processes C and E, the execution of Process C is prioritized. Therefore, an operation command is generated that causes Process C to be performed on the two microtubes, and then Process E to be performed on another one micro tube. However, the process symbol 103 in which "A" is written and the process symbol 103 in which "D" is written are arranged in the second direction orthogonal to the first direction (direction indicating a consecutive process), and hence the instruction of a consecutive process for Processes A and B and the instruction for performing Process D after Process A are incompatible with each other.

The consecutive/general judgment unit 16c of this embodiment is configured to judge, based on the protocol chart acquired by the protocol chart acquisition unit 11, whether or not the group of the process symbols for which a consecutive process is specified and another process symbol are arranged in a direction orthogonal to the direction indicating a consecutive process. In the case of the protocol chart of the third example, the consecutive/general judgment unit 16c judges that the group of the process symbols 103 for which a consecutive process is specified (i.e., the process symbol 103 in which "A" is written and the process symbol 103 in which "B" is written) and another process symbol 103 (i.e., the process symbol 103 in which "D" is written) are arranged in a direction orthogonal to (i.e., horizontal direction of the protocol chart illustrated in FIG. 10) the direction indicating a consecutive process.

In response to the judgment by the consecutive/general judgment unit 16c, the warning unit 20 warns the user of the operation command generation device 1 by, for example, displaying a warning message on the monitor 1h. The warning unit 20 may issue the warning when the job generation unit 13 generates a job.

With the operation command generation device 1 according to this embodiment, interference between the consecutive processes and the general processes is prevented by issuing a warning when the specification of the consecutive processes and the specification of the general processes are incompatible. In response to the warning of interference between the consecutive processes and the general processes, the user of the operation command generation device 1 can edit the protocol chart to write a protocol that does not have any contradict ions. The user of the operation command generation device 1 can also freely edit the protocol chart without unnecessary warnings until a job is generated.

Figure 11:
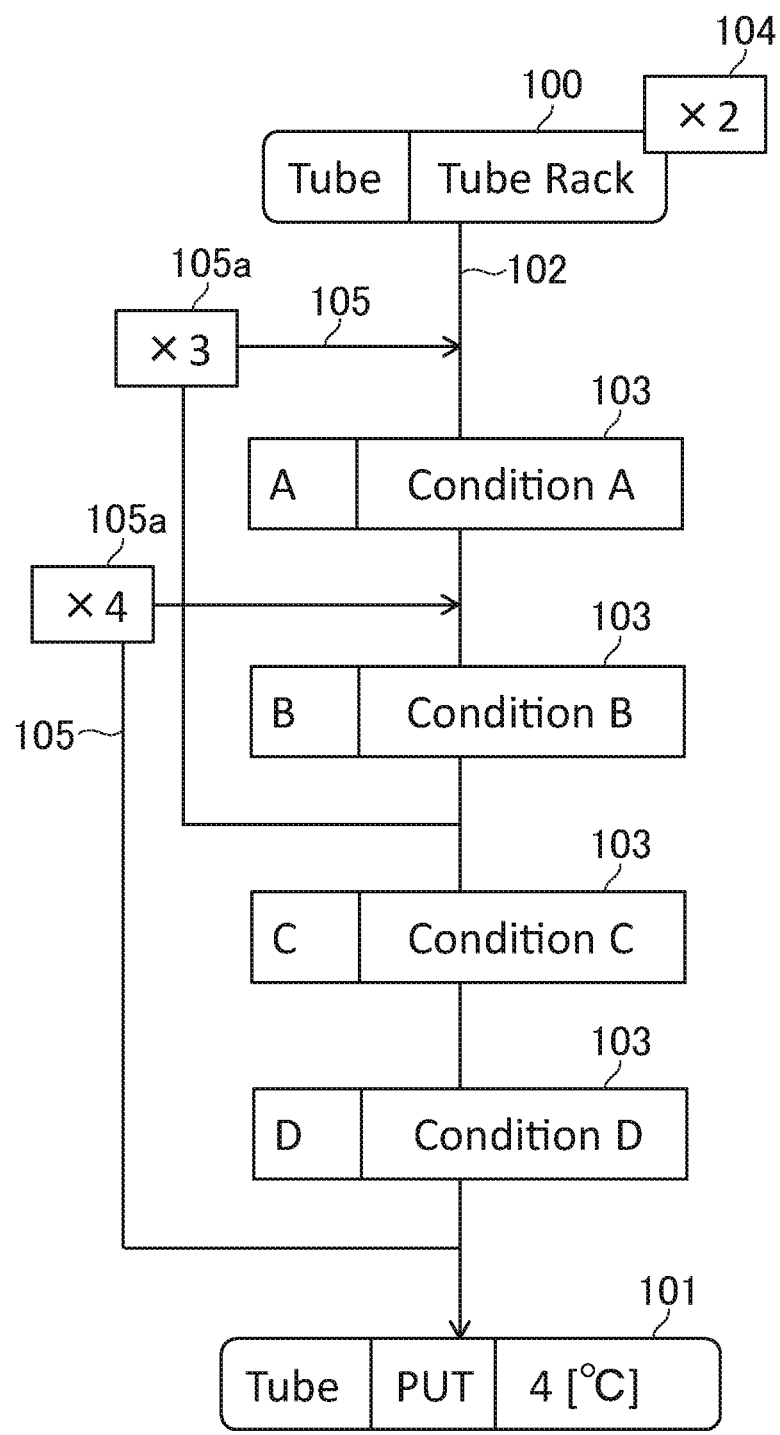
FIG. 11 is a diagram for illustrating a fourth example of a protocol chart on which a warning is to be displayed by the operation command generation device according to the embodiment of the present invention.

FIG. 11 is a diagram for illustrating a fourth example of a protocol chart on which a warning is to be displayed by the operation command generation device 1 according to the embodiment of the present invention. In the protocol chart illustrated in FIG. 11, two iteration lines 105 are arranged, namely, an iteration line 105 associated with the iteration count symbol 105a in which "×3" is displayed and an iteration line 105 associated with the iteration count symbol 105a in which "×4" is displayed.

In the protocol chart of the fourth example, the group of the process symbols 103 for which an iterative process is specified (i.e., the process symbol 103 in which "A" is written and the process symbol 103 in which "B" is written) and the group of the process symbols 103 for which another iterative process is specified (i.e., the process symbol 103 in which "B" is written, the process symbol 103 in which "C" is written, and the process symbol 103 in which "D" is written) are partially duplicated in terms of the process symbol 103 in which "B" is written. In this case, the instruction of causing Processes A and B to be repeatedly performed three times and the instruction of causing Processes B, C, and D to be repeatedly performed four times are incompatible.

The iterative/iterative judgment unit 16d of this embodiment is configured to judge, based on the protocol chart acquired by the protocol chart acquisition unit 11, whether or not two groups of process symbols for which an iterative process is specified partially duplicate each other. In the case of the protocol chart of the fourth example, the iterative/iterative judgment unit 16d judges that a group of the process symbols for which an iterative process is specified (i.e., the process symbol 103 in which "A" is written and the process symbol 103 in which "B" is written) and another group of the process symbols for which an iterative process is specified (i.e., the process symbol 103 in which "B" is written, the process symbol 103 in which "C" is written, and the process symbol 103 in which "D" is written) partially duplicate each other.

In response to the judgment by the iterative/iterative judgment unit 16d, the warning unit 20 warns the user of the operation command generation device 1 by, for example, displaying a warning message on the monitor 1b. The warning unit 20 may issue the warning when the job generation unit 13 generates a job.

With the operation command generation device 1 according to this embodiment, interference among iterative processes is prevented by issuing a warning when two iterative processes that are partially duplicated are specified. In response to the warning of interference among iterative processes, the user of the operation command generation device 1 can edit the protocol chart to write a protocol that does not have any contradictions. The user of the operation command generation device 1 can also freely edit the protocol chart without unnecessary warnings until a job is generated.

Each of the configurations in the embodiment above is described as a specific example, and the invention disclosed in the present application is not intended to be limited to those specific configurations themselves. Various modifications may be made by a person skilled in the art to the disclosed embodiment. For example, the functions, the operation method, and the like may be appropriately changed and added. Further, the control illustrated in the flowcharts may also be appropriately replaced by one having equivalent functions. It should be understood that the technical scope of the invention disclosed in the present application cover all such modifications.

In other words, it should be understood by those skilled in the art that various modifications, combinations, sub-combinations and alterations may occur depending on design requirements and other factors insofar as they are within the scope of the appended claims or the equivalents thereof.

The invention claimed is:

1. An operation command generation device, which is configured to generate an operation command, which is a collection of jobs to be performed by a process system of at least a robot, based on a protocol chart of at least a plurality of process symbols each representing a process to be performed on a container in which a process subject is stored, the operation command generation device circuitry comprising at least one processor configured to:
   generate, based on the protocol chart, a job for each process indicated by each of the plurality of process symbols;
   instruct a priority condition for determining a job execution order;
   determine, when there are a plurality of containers, an execution order of the jobs based on the priority by using at least a first and second condition, where the first condition is that each job corresponding to each of the plurality of process symbols is to be repeatedly executed the same number of times as a count of the plurality of containers; and wherein the second condition is that each job corresponding to each of the plurality of process symbols is to be executed in an order corresponding to an arrangement order of each of the plurality of process symbols in the protocol chart;
   instruct the first condition to be prioritized over the second condition;
   instruct, for a plurality of process symbols for which a consecutive process is specified, the second condition to be prioritized over the first condition; and
   generate, for one or more process symbols for which an iterative process is specified, a job corresponding to each of the one or more process symbols, a number of jobs to be generated being equal to an iteration count;
   wherein the operation command generation device further comprises a third condition wherein a job corresponding to a process symbol for which an iterative process is specified is to be repeatedly executed the same number of times as a collectively-specified iteration count, and
   wherein the at least one processor is further configured to:
   instruct the first condition and the second condition to be prioritized over the third condition; and
   issue a warning when a group of process symbols, for which a consecutive process is specified and a group of process symbols for which an iterative process is specified, partially duplicate each other.

2. The operation command generation device according to claim 1, wherein the at least one processor issues a warning when the group of process symbols, for which a consecutive process is specified and another process symbol, are arranged in a direction orthogonal to a direction indicating the consecutive process.

3. The operation command generation device according to claim 1, wherein at least one processor sues a warning when a job is generated.

4. The operation command generation device according to claim 1, wherein the jobs to be generated comprise:
   a first level job comprising a command for repeating, the same number of times as a container count, a group of processes for which a consecutive process is specified, and a command for repeating, the same number of times as an iteration count, a group of processes for which an iterative process is specified, and
   a second level job comprising a command for repeating, the same number of times as the container count, individual processes other than the group of processes for which a consecutive process is specified, and a command for performing once the group of processes for which a consecutive process is specified.

5. The operation command generation device according to claim 1, wherein the at least one processor issues a warning when two groups of process symbols, for which an iterative process is specified, partially duplicate each other.

6. The operation command generation device according to claim 5, wherein the at least one processor issues a warning when the group of process symbols, for which a consecutive process is specified and another process symbol, are arranged in a direction orthogonal to a direction indicating the consecutive process.

7. The operation command generation device according to claim 1, wherein at least one processor issues a warning when a group of process symbols for which a consecutive process is specified includes or is included by a group of process symbols for which a non-consecutive process is specified.

8. The operation command generation device according to claim 7, wherein the at least one processor issues a warning when the group of process symbols, for which a consecutive process is specified and another process symbol, are arranged in a direction orthogonal to a direction indicating the consecutive process.

9. The operation command generation device according to claim 7, wherein the at least one processor issues a warning when two groups of process symbols, for which an iterative process is specified, partially duplicate each other.

10. The operation command generation device according to claim 9, wherein the at least one processor issues a warning when the group of process symbols, for which a consecutive process is specified and another process symbol, are arranged in a direction orthogonal to a direction indicating the consecutive process.

11. An operation command generation method for generating an operation command, which is a collection of jobs to be performed by a process system of at least a robot, based on a protocol chart of at least a plurality of process symbols each representing a process to be performed on a container in which a process subject is stored, the operation command generation method comprising:
  generating, based on the protocol chart, a job for each process indicated by each of the plurality of process symbols;
  instructing a priority of a condition for determining a job execution order;
  determining, when there are a plurality of containers, an execution order of the jobs based on the instructed priority by using a first condition and a second condition, wherein the first condition is that each job corresponding to each of the plurality of process symbols is to be repeatedly executed the same number of times as a count of the plurality of containers; and the second condition is that each job corresponding to each of the plurality of process symbols is to be executed in an order corresponding to an arrangement order of each of the plurality of process symbols in the protocol chart;
  instructing the first condition to be prioritized over the second condition;
  instructing, for a plurality of process symbols for which a consecutive process is specified, the second condition to be prioritized over the first condition; and
  generating, for one or more process symbols for which an iterative process is specified, a job corresponding to each of the one or more process symbols, a number of jobs to be generated being equal to an iteration count;
  wherein the operation command generation method further comprises a third condition wherein a job corresponding to a process symbol for which an iterative process is specified is to be repeatedly executed the same number of times as a collectively-specified iteration count, and
  wherein the operation command generation method further comprises:
    instructing the first condition and the second condition to be prioritized over the third condition; and
    issuing a warning when a group of process symbols, for which a consecutive process is specified and a group of process symbols for which an iterative process is specified, partially duplicate each other.

12. A system comprising:
  an operation command generation device which causes a computer to generate an operation command, which is a collection of jobs to be performed by a process system of at least a robot, based on a protocol chart of at least a plurality of process symbols each representing a process to be performed on a container in which a process subject is stored, the operation command generation device circuitry comprising at least one processor configured to:
    generate, based on the protocol chart, a job for each process indicated by each of the plurality of process symbols;
    instruct a priority condition for determining a job execution order;
    determine, when there are a plurality of containers, an execution order of the jobs based on the priority by using at least a first and second condition, where the first condition is that each job corresponding to each of the plurality of process symbols is to be repeatedly executed the same number of times as a count of the plurality of containers; and wherein the second condition is that each job corresponding to each of the plurality of process symbols is to be executed in an order corresponding to an arrangement order of each of the plurality of process symbols in the protocol chart;
    instruct the first condition to be prioritized over the second condition:
    instruct, for a plurality of process symbols for which a consecutive process is specified, the second condition to be prioritized over the first condition; and
    generate, for one or more process symbols for which an iterative process is specified, a job corresponding to each of the one or more process symbols, a number of jobs to be generated being equal to an iteration count:
  wherein the operation command generation device further comprises:
    a robot controller configured to control a control subject based on an operation command generated by the operation command generation device; and
    a robot configured to perform a process on a process subject with one or more arms, the robot being included in control subjects of the robot controller
  wherein the operation command generation device further comprises a third condition wherein a job corresponding to a process symbol for which an iterative process is specified is to be repeatedly executed the same number of times as a collectively-specified iteration count, and
  wherein the at least one processor is further configured to:
    instruct the first condition and the second condition to be prioritized over the third condition; and
    issue a warning when a group of process symbols, for which a consecutive process is specified and a group of process symbols for which an iterative process is specified, partially duplicate each other.

* * * * *